Oct. 7, 1958 F. MEILLAND Plant Pat. 1,758
ROSE PLANT
Filed Feb. 26, 1958
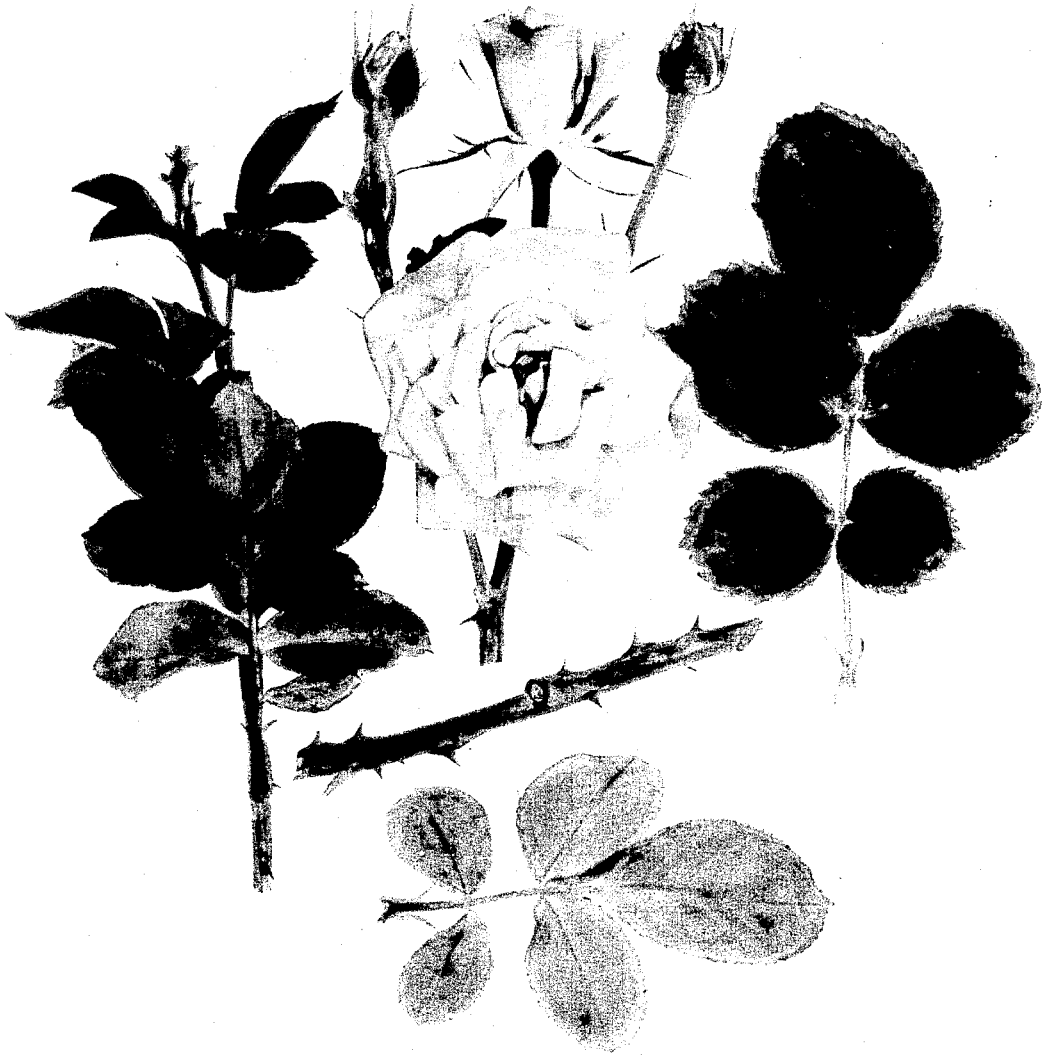
Inventor.
Francis Meilland
By: Robb & Robb
Attorneys.

United States Patent Office

Plant Pat. 1,758
Patented Oct. 7, 1958

1,758

ROSE PLANT

Francis Meilland, Cap d'Antibes, Alpes Maritimes, France, assignor to The Conard-Pyle Company, West Grove, Pa., a corporation of Pennsylvania Application February 26, 1958, Serial No. 717,796

Claims priority, application France July 29, 1957

1 Claim. (Cl. 47—61)

The present invention relates to a new and distinct variety of rose plant of the hybrid polyantha class, which was originated by me by crossing the variety "Moulin Rouge" (U. S. Plant Patent No. 1,298) with the variety "Fashion" (U. S. Plant Patent No. 789).

The primary objective in making this cross was to produce a new variety of rose plant which combines the best characteristics of the parent varieties aforesaid. This objective was fully achieved, along with the attainment of other improvements, as evidenced by the following combination of outstanding characteristics which distinguish the new variety from its parents, as well as from all other varieties of which I am aware:

(1) Exceptional vigor, accompanied by an outstandingly compact and uniform habit of growth which is unusual for such a strong-growing plant;

(2) Very good, dark green foliage which has better than average resistance to blackspot, and serves to accentuate the brilliancy of the flower color;

(3) Excellent floriferousness;

(4) Very double, well-formed blooms; and (5) An Iridescent Scarlet general color tonality of the blooms which is a unique color and not found in any other rose presently in commerce.

Asexual reproduction of the new variety by budding, as performed in France and at West Grove, Pennsylvania, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with The Horticultural Color Chart of the Royal Horticultural Society, except where general color terms of ordinary dictionary significance are obvious:

Type: Hardy; bush; outdoor; seedling; for cut flowers and for garden decoration.

Class: Hybrid polyantha.

Breeding: Seedling.

*Seed parent.*—"Moulin Rouge."

*Pollen parent.*—"Fashion."

Propagation: Holds its distinguishing characteristics through succeeding propagations by budding.

*Flower*

Locality where grown and observed: West Grove, Pennsylvania, U. S. A.

Flowers borne: Several to stem; in regular cluster; on stems of medium length and normal strength.

Quantity of bloom: Abundant, outdoors.

Continuity: Continuous.

Fragrance: Moderate. Nature—musk.

Bud:

*Peduncle.*—Medium length; medium caliper; erect; rough; with medium number of red hairs. Color—reddish.

*Before calyx breaks.*—Size—small. Form—medium long; ovoid; with a conspicuous neck; with foliaceous appendages on the surface of the bud; with slender, bristle-like foliaceous parts extending beyond the tip of the bud equal to ¼ or more of its length.

*As calyx breaks.*—Color—Currant Red, Plate 821.

*As first petal opens.*—Size—medium. Form—pointed ovoid. Color: outside—Blood Red, Plate 820/1, dotted and blotched where first exposed to light with Oxblood Red, Plate 00823, with point of attachment Pea Green, Plate 61/3; inside—Iridescent Dutch Vermilion, Plate 717, evenly distributed except for point of attachment which is Dresden Yellow, Plate 64/3.

*Opening.*—Opens up well.

Bloom:

*Size (when fully open).*—From 2 inches to 2½ inches.

*Petalage.*—Very double; from 45 to 50 petals; arranged regularly.

*Form.*—Full and high-centered at first, but becoming flat; petals being at first loosely rolled outward, and remaining loosely rolled outward at maturity.

Petals: Leathery; thick; with inside velvety and outside satiny.

*Shape.* — Outer — round-obovate. Intermediate — obovate. Inner—obovate.

This description of a newly opened flower was made from a rose grown outdoors in the month of August, at West Grove, Pennsylvania, U. S. A.:

*Color.*—Outer petal: outside surface—Currant Red, Plate 821/1, with point of attachment Pea Green, Plate 61/3; inside surface—Iridescent Scarlet, Plate 19, with point of attachment Pea Green, Plate 61/2. Intermediate petal: outside surface—Currant Red, Plate 821/1, with point of attachment Pea Green, Plate 61/3; inside surface—Iridescent Signal Red, Plate 719, with point of attachment Pea Green, Plate 61/2. Inner petal: outside surface—Cardinal Red, Plate 822, with point of attachment Pea Green, Plate 61/3; inside surface—Iridescent Orient Red, Plate 819, with point of attachment Pea Green, Plate 61/2.

This description was made from a rose that was open for 3 days outdoors in the month of August, at West Grove, Pennsylvania, U. S. A.:

*Color.*—Outer petal: outside surface—Claret Rose, Plate 021, with point of attachment Pea Green, Plate 61/3; inside surface—Scarlet, Plate 19, shading to Camellia Rose, Plate 622/1 at base of petal, with point of attachment Pea Green, Plate 61/3. Inner petal: outside surface—Claret Rose, Plate 021, with point of attachment Pea Green, Plate 61/3; inside surface—Scarlet, Plate 19, with point of attachment Pea Green, Plate 61/3, surrounded by a narrow border of Camellia Rose, Plate 622/1.

*General color effect.*—Newly opened flower—Iridescent Scarlet, Plate 19, with reverse of petals showing Currant Red, Plate 821/1. 3-days open—Scarlet, Plate 19.

*Behavior.*—Drop off cleanly.

*Flower longevity.*—On bush in garden—5 days in August. Cut roses grown outdoors and kept at living room temperatures—4 days in August.

*Reproductive organs*

Stamens: Medium number; arranged regularly about pistils; mixed with petaloids.
Filaments: Many; most with anthers; medium length. Color—Uranium Green, Plate 63/2.
Anthers: All open at once; occasionally an anther fused with a petaloid. Color—Indian Yellow, Plate 6.
Pollen: Moderate abundance. Color—gold.
Pistils: Medium number.
Styles: Uneven; medium length; medium caliper; bunched.
Stigma: Color—whitish yellow.
Ovaries: Some protruding from receptacle.
Hips: None.
Sepals: Permanent; medium length; spear-shaped.
Seeds: None.

*Plant*

Foliage:

*Leaves.*—Compound of 5 leaflets; from normal abundance to abundant; medium size; moderately leathery.

*Leaflets.*—Shape—oval, with apex acute. Base—obtuse. Margin—simply serrate.

*Color.*—Mature: upper surface—Spinach Green, Plate 0960; under surface—Spinach Green, Plate 0960/2. Young: upper surface—Maroon, Plate 1030, blotched here and there with Spinach Green, Plate 0960; under surface—Maroon, Plate 1030, washed with Spinach Green, Plate 0960/2.

*Rachis (the supporting stem of the compound leaf).*—Medium caliper. Upper side—hairy. Under side—sparsely prickly.

*Stipules.*—Medium length; narrow; with points of medium length turning out at an angle of more than 45°.

*Disease resistance.*—Better than average resistance to blackspot and average resistance to mildew, as compared with other varieties grown under the same cultural conditions at West Grove, Pennsylvania, U. S. A.

Growth:

*Habit.*—Bushy; much-branched.

*Growth.*—Vigorous.

*Canes.*—Medium caliper.

*Main stems.*—Bright. Color—Spinach Green, Plate 0960/1. Prickles—several; color—Garnet Brown, Plate 00918/3 at base, with tips showing Fern Green, Plate 0862. Hairs—none.

*Branches.*—Bright. Color—Spinach Green, Plate 0960/1. Prickles—several; color—Garnet Brown, Plate 00918/3, overlying Fern Green, Plate 0862. Hairs—none.

*New shoots.*—Dull. Color—Lettuce Green, Plate 861/2, overlaid with Garnet Brown, Plate 00918/3. Prickles—several; color—Garnet Brown, Plate 00918/3. Hairs—none.

I claim:

A new and distinct variety of rose plant of the hybrid polyantha class, substantially as herein shown and described, characterized particularly as to novelty by the unique combination of its exceptional vigor, compact and uniform habit, very good dark green foliage which has better than average resistance to blackspot and serves to accentuate the brilliancy of the flower color, excellent floriferousness and very double, well-formed blooms of Iridescent Scarlet general color tonality.

No references cited.